United States Patent
Trepagnier et al.

(10) Patent No.: US 11,155,864 B2
(45) Date of Patent: Oct. 26, 2021

(54) ORTHOGONAL DEBLOCKING OF NUCLEOTIDES

(71) Applicant: Illumina, Inc., San Diego, CA (US)

(72) Inventors: Eliane H Trepagnier, San Diego, CA (US); Tarun Khurana, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 364 days.

(21) Appl. No.: 15/739,587

(22) PCT Filed: Jul. 8, 2016

(86) PCT No.: PCT/US2016/041568
§ 371 (c)(1),
(2) Date: Dec. 22, 2017

(87) PCT Pub. No.: WO2017/019278
PCT Pub. Date: Feb. 2, 2017

(65) Prior Publication Data
US 2018/0312917 A1 Nov. 1, 2018

Related U.S. Application Data

(63) Continuation of application No. 62/198,947, filed on Jul. 30, 2015.

(51) Int. Cl.
*C12Q 1/68* (2018.01)
*C12Q 1/6874* (2018.01)

(52) U.S. Cl.
CPC .................... *C12Q 1/6874* (2013.01)

(58) Field of Classification Search
CPC .................................................. C12Q 1/874
See application file for complete search history.

(56) References Cited

U.S. PATENT DOCUMENTS

| | | | | |
|---|---|---|---|---|
| 7,244,567 B2 * | 7/2007 | Chen | .................. | C12Q 1/6844 435/6.11 |
| 7,329,496 B2 | 2/2008 | Dower et al. | | |
| 7,754,429 B2 * | 7/2010 | Rigatti | ............... | C12Q 21/6874 435/6.1 |
| 10,378,051 B2 * | 8/2019 | Meuleman | ............ | C12Q 1/6874 |
| 2007/0128624 A1 | 6/2007 | Gormley et al. | | |
| 2011/0014611 A1 | 1/2011 | Ju et al. | | |
| 2013/0085073 A1 * | 4/2013 | Meuleman | ............ | C12Q 1/6874 506/2 |
| 2015/0031560 A1 * | 1/2015 | Fabani | ................... | C07H 21/04 506/4 |
| 2015/0080232 A1 | 3/2015 | Ju et al. | | |

FOREIGN PATENT DOCUMENTS

| | | | | |
|---|---|---|---|---|
| EP | 1594981 A2 * | 11/2005 | ......... | C12N 15/1093 |
| EP | 1 590 477 B1 | 7/2009 | | |
| EP | 2652153 A2 | 10/2013 | | |
| EP | 3293272 A1 * | 3/2018 | .......... | C12Q 1/6874 |
| WO | 2005/003375 A2 | 1/2005 | | |
| WO | 2007/048033 A1 | 4/2007 | | |
| WO | 2009/086353 A1 | 7/2009 | | |
| WO | WO-2009086353 A1 * | 7/2009 | ....... | C12Q 2525/186 |
| WO | 2012/050920 A1 | 4/2012 | | |
| WO | 2015/002789 A1 | 1/2015 | | |

OTHER PUBLICATIONS

Guo J, Yu L, Turro NJ, Ju J. An integrated system for DNA sequencing by synthesis using novel nucleotide analogues. Acc Chem Res. 2010; 43(4):551-563. (Year: 2010).*
Seroz, Thierry, Authorized Officer, European Patent Office, International Search Report, International Patent Application No. PCT/US2016/041568, dated Sep. 23, 2016, 3 pages.
Foldesi et al., "The fluoride cleavable 2-(cyanoethoxy)methyl (CEM) group as reversible 3'-0-terminator for DNA sequencing-by-synthesis—synthesis, incorporation, and cleavage", Nucleosides, Nucleotides and Nucleic Acids, vol. 26, No. 3, 2007, pp. 271-275.
Turcatti et al., "A new class of cleavable fluorescent nucleotides: synthesis and optimization as reversible terminators for DNA sequencing by synthesis", Nucleic Acides Research, vol. 36, No. 4, 2008, pp. E25-1.
Seroz, Thierry, Communication Pursuant to Article 94(3) EPC, European Patent Office, Application No. 16739665.4, dated May 21, 2019.
Anikaev, A.Y. et al., "Clinical applications of next-generation sequencing (NGS)", Laboratory service, 2014, 1:32-36.

* cited by examiner

Primary Examiner — Gary Benzion
Assistant Examiner — Olayinka A Oyeyemi
(74) *Attorney, Agent, or Firm* — Gavrilovich, Dodd & Lindsey LLP

(57) ABSTRACT

A method including steps of (a) providing an array of sites, wherein each site comprises a mixture of different nucleic acid templates; (b) extending primers hybridized to the different nucleic acid templates at each of the sites with different nucleotide analogs having different reversible blocking moieties, respectively, thereby producing different primer extension products at each site; (c) detecting the different primer extension products to distinguish the different nucleotide analogs at each site; and (d) removing the different reversible blocking moieties from the primer extension products at each of the sites using a first treatment that is selective for a first of the different reversible blocking moieties and a second treatment that is selective for a second of the different reversible blocking moieties.

36 Claims, 2 Drawing Sheets

FIG. 1

| Simultaneous Sequencing of R1 and R2 Templates | | | |
|---|---|---|---|
| Array Treatment | R1 Template Response | R2 Template Response | |
| Deliver R1 primer-block1 and R2 primer | hybridize R1 primer-block1 | hybridize R2 primer (no block) | First cycle |
| Deliver dNTP-block2-label2 | | incorporate dNTP-block2-label2 | |
| Expose to block1 cleavage | cleave block1 | | |
| Deliver dNTP-block1-label1 | incorporate dNTP-block1-label1 | | |
| First base read R1 and R2 | Detect label1 & label2 | | |
| Expose to block2 cleavage and label2 cleavage | | cleave block2 & label2 | Second cycle |
| Deliver dNTP-block2-label2 | | incorporate dNTP-block2-label2 | |
| Expose to block1 cleavage and label1 cleavage | cleave block1 & label1 | | |
| Deliver dNTP-block1-label1 | incorporate dNTP-block1-label1 | | |
| Second base read R1 and R2 | Detect label1 & label2 | | |
| Expose to block2 cleavage and label2 cleavage | | cleave block2 & label2 | Third Cycle |
| Deliver dNTP-block2-label2 | | incorporate dNTP-block2-label2 | |
| Expose to block1 cleavage and label1 cleavage | cleave block1 & label1 | | |
| Deliver dNTP-block1-label1 | incorporate dNTP-block1-label1 | | |
| Third base read R1 and R2 | Detect label1 & label2 | | |

FIG. 2

| Simultaneous Sequencing of R1 and R2 Templates | | | |
|---|---|---|---|
| Array Treatment | R1 Template Response | R2 Template Response | |
| Deliver R1 primer-block1 and R2 primer | hybridize R1 primer-block1 | hybridize R2 primer (no block) | First cycle |
| Deliver dNTP-block2-label2 | | incorporate dNTP-block2-label2 | |
| Expose to block1 cleavage | cleave block1 | | |
| Deliver dNTP-block1-label1 | incorporate dNTP-block1-label1 | | |
| Expose to block2 cleavage | | cleave block2 | |
| First base read R1 and R2 | Detect label1 & label2 | | |
| Expose to label1 cleavage and label2 cleavage | cleave label1 | cleave label2 | Second cycle |
| Deliver dNTP-block2-label2 | | incorporate dNTP-block2-label2 | |
| Expose to block1 cleavage | cleave block1 | | |
| Deliver dNTP-block1-label1 | incorporate dNTP-block1-label1 | | |
| Expose to block2 cleavage | | cleave block2 | |
| Second base read R1 and R2 | Detect label1 & label2 | | |
| Expose to label1 cleavage and label2 cleavage | cleave label1 | cleave label2 | Third cycle |
| Deliver dNTP-block2-label2 | | incorporate dNTP-block2-label2 | |
| Expose to block1 cleavage | cleave block1 | | |
| Deliver dNTP-block1-label1 | incorporate dNTP-block1-label1 | | |
| Expose to block2 cleavage | | cleave block2 | |
| Third base read R1 and R2 | Detect label1 & label2 | | |

ORTHOGONAL DEBLOCKING OF NUCLEOTIDES

CROSS REFERENCE TO RELATED APPLICATION

This patent document is a 35 U.S.C. § 371 National Stage application of, and claims the benefits and priority of International Patent Application No. PCT/US2016/041568, filed on Jul. 8, 2016, which further claims the benefits and priority of U.S. Provisional Patent Application No. 62/198,947, filed on Jul. 30, 2015. The entire disclosures of the above applications are incorporated by reference in their entirety as part of this document.

BACKGROUND

This disclosure relates generally to nucleic acid analysis, and more specifically to nucleic acid sequencing.

Currently available commercial platforms for sequencing DNA are relatively costly. These platforms use a 'sequencing-by-synthesis' approach, so called because DNA polymers are synthesized while detecting the addition of each monomer (i.e. nucleotide) to the growing polymer structure. Because a template DNA strand strictly directs synthesis of a new DNA polymer, one can infer the sequence of the template DNA from the series of nucleotide monomers that were added to the growing strand during the synthesis. The ability to detect monomer additions is facilitated by specially engineered variants of the biochemical components that normally carry out DNA synthesis in biological systems. These engineered components are relatively expensive to make and are consumed in relatively large amounts during sequencing-by-synthesis. Furthermore, monitoring the reaction uses relatively expensive hardware such as lasers, detection optics and complex fluid delivery systems. The most successful commercial platforms to date also require expensive reagents and hardware to amplify the DNA templates before sequencing-by-synthesis can even begin. The complexity and expense of these platforms has hindered their use in some clinical and research contexts where there is a clear need for the technology.

Thus, there exists a need for improvements to sequencing-by-synthesis platforms to make them more cost effective, rapid and convenient. The present disclosure addresses this need and provides other advantages as well.

BRIEF SUMMARY

The present disclosure provides a method for identifying nucleic acid templates. The method can include steps of (a) providing an array of sites, wherein each site comprises a mixture of at least two different nucleic acid templates; (b) extending primers hybridized to the different nucleic acid templates at each of the sites with different nucleotide analogs having different reversible blocking moieties, respectively, thereby producing different primer extension products at each site; (c) detecting the different primer extension products to distinguish the different nucleotide analogs at each site; and (d) removing the different reversible blocking moieties from the primer extension products at each of the sites using a first treatment that is selective for a first of the different reversible blocking moieties and a second treatment that is selective for a second of the different reversible blocking moieties. Optionally, the method can further include (e) repeating (b) through (d) to determine the sequence of different nucleotide analogs added to each of the different extension products at each of the sites.

Also provided is a method for sequencing nucleic acid templates that can include the steps of (a) providing an array of sites, wherein each site includes a first nucleic acid template and a second nucleic acid template, wherein the first nucleic acid template has a sequence that is different from the sequence of the second nucleic acid template, wherein a first primer is bound to the first nucleic acid template, and wherein a second primer is bound to the second nucleic acid template, a reversible blocking moiety being attached to the second primer; (b) extending the first primer by addition of a first nucleotide analog that is attached to a reversible blocking moiety, wherein the reversible blocking moiety that is attached to the first nucleotide is different from the reversible blocking moiety that is attached to the second primer; (c) selectively removing the reversible blocking moiety that is attached to the second primer while retaining the reversible blocking moiety that is attached to the nucleotide analog that is added to the first primer; (d) extending the second primer by addition of a second nucleotide analog that is attached to a reversible blocking moiety, wherein the reversible blocking moiety that is attached to the first nucleotide analog is different from the reversible blocking moiety that is attached to the second nucleotide analog; and (e) detecting the nucleotide analog that is added to the first primer and the nucleotide analog that is added to the second primer, at each of the sites, thereby determining the different sequences of the first template and the second template at each of the sites. Optionally, the method can further include steps of (f) selectively removing the reversible blocking moiety that is attached to the first nucleotide analog that is added to the first primer while retaining the reversible blocking moiety that is attached to the second nucleotide analog that is added to the second primer; (g) extending the first primer, after (f), by addition of a third nucleotide analog that is attached to a reversible blocking moiety; (h) selectively removing the reversible blocking moiety that is attached to the second nucleotide analog that is added to the second primer while retaining the reversible blocking moiety that is attached to the first nucleotide analog that is added to the first primer; (i) extending the second primer, after (h), by addition of a fourth nucleotide analog that is attached to a reversible blocking moiety, wherein the reversible blocking moiety that is attached to the third nucleotide analog is different from the reversible blocking moiety that is attached to the fourth nucleotide analog; and (h) detecting the nucleotide analog that is added to the first primer in (g) and the nucleotide analog that is added to the second prime in (i), at each of the sites, thereby determining the different sequences of the first template and the second template at each of the sites. Optionally, steps (f) through (h) can be repeated.

Also provided is a method for sequencing nucleic acid templates that can include the steps of (a) providing an array of sites, wherein each site includes a first nucleic acid template and a second nucleic acid template, wherein the first nucleic acid template has a sequence that is different from the sequence of the second nucleic acid template, wherein a first primer is bound to the first nucleic acid template, a reversible blocking moiety being attached to the first primer, wherein a second primer is bound to the second nucleic acid template, a reversible blocking moiety being attached to the second primer, and wherein the reversible blocking moiety that is attached to the first primer is different from the reversible blocking moiety that is attached to the second primer; (b) selectively removing the reversible blocking moiety that is attached to the first primer while retaining the reversible blocking moiety that is attached to the second primer; (c) extending the first primer by addition of a first nucleotide analog that is attached to a reversible blocking moiety; (d) selectively removing the reversible blocking moiety that is attached to the second primer while retaining the reversible blocking moiety that is attached to the nucleotide analog that is added to the first primer; (e) extending the second primer by addition of a second nucleotide analog that is attached to a reversible blocking moiety, wherein the reversible blocking moiety that is attached to the first nucleotide analog is different from the reversible blocking moiety that is attached to the second nucleotide analog; and (f) detecting the nucleotide analog that is added to the first primer and the nucleotide analog that is added to the second primer, at each of the sites, thereby determining the different sequences of the first template and the second template at each of the sites.

The present disclosure further provides a nucleic acid array that includes a plurality of sites on a solid support, wherein each site includes a first nucleic acid template and a second nucleic acid template, wherein the first nucleic acid template has a sequence that is different from the sequence of the second nucleic acid template, wherein a first primer is bound to the first nucleic acid template, a first reversible blocking moiety being attached to the first primer, wherein a second primer is bound to the second nucleic acid template, a second reversible blocking moiety being attached to the second primer, and wherein the first reversible blocking moiety is different from the second reversible blocking moiety.

BRIEF DESCRIPTION OF THE DRAWINGS

FIG. 1 shows a cycle diagram for sequencing by synthesis carried out simultaneously for a mixture of two templates at a site of an array, wherein subsets of label moieties and deblocking moieties that are present on the same extension products are cleaved simultaneously.

FIG. 2 shows a cycle diagram for sequencing by synthesis carried out simultaneously for a mixture of two templates at a site of an array, wherein label moieties that are present on different extension products (i.e. produced in both R1 and R2 reactions) are cleaved simultaneously.

DETAILED DESCRIPTION

This disclosure provides a method for high density detection of nucleic acids. Particular embodiments of the methods of the present disclosure exploit known techniques for manipulating and detecting nucleic acids. However, improvements set forth below provide orthogonal processing such that the density of information obtained from use of these techniques is increased.

The example of a primer extension-based detection technique is illustrative of the increased density of information that can be obtained. Specifically, a target sequence of a nucleic acid can be hybridized to a primer and the primer extended by a DNA polymerase to add a labeled nucleotide analog. An array format can be used with multiple sites, each site having a single target sequence that differs from the target sequences present at other sites. Optionally several different nucleotide analog species, each having a distinguishable label, are used as well. Primer extension results in recruitment of the labeled nucleotide analog to the nucleic acid having the target sequence. In an array format, where different labeled nucleotide analogs are used, one can distinguish the label that is recruited to each site, and use this information to identify the target nucleic acid at that site. The density of information obtained from this array format is one target sequence identified per site.

In an orthogonal format of the present disclosure, each site of the array can contain a mixture of two or more different target sequences that are simultaneously treated (e.g. with chemical reagents or physical manipulations) and simultaneously observed (e.g. with a detector having resolution that is too low to spatially resolve nucleic acids in the mixture). Nonetheless, the orthogonal treatments set forth herein produce differential effects that allow the different target sequences to be distinguishable from each other. In this case the information derived from the array can be at least doubled. Two different primers can be delivered to an array and due to differential complementary they will hybridize to the two different template sequences, respectively, at each individual site. The first primer can have a first reversible blocking moiety that prevents it from being extended until a first deblocking treatment is applied, and the second primer can have a second reversible blocking moiety that prevents it from being extended until a second deblocking treatment is applied. In this example, the first deblocking treatment is selective for the first reversible blocking moiety compared to a second reversible blocking moiety and the second deblocking treatment is selective for the second reversible blocking moiety compared to the first reversible blocking moiety. This selective deblocking capability provides orthogonality such that the primers, although being exposed to each deblocking treatment, can be individually modified for extension and detection. Thus the two primers, and more significantly the templates that direct their extension, can be distinguished by this chemical switching even though the molecules themselves may not be separated sufficiently to allow spatial distinction using detection system in use.

The concepts of orthogonality exemplified above for a primer extension-based detection technique can be readily applied to a sequencing-by-synthesis (SBS) technique. An exemplary cycle diagram for orthogonal SBS for two templates (R1 and R2) at a site is shown in FIG. 1. The first column in the diagram represents a treatment to which the array is exposed (i.e. both of the templates are exposed to the treatment). The second and third columns indicate the effect of the treatment on the first template and second template, respectively. In the first step of the first cycle, a mixture of primers is contacted with the array which results in hybridization to respective primer binding sites. Following step 1, the R1 primer that is hybridized to the R1 template is blocked by block1 and the R2 primer lacks a blocking group (optionally primer R2 can be blocked by an orthogonal blocking moiety, block2). As such, the two primers can be separately extended. For example, in the second step of the first cycle, a nucleotide having block2 and label2 is delivered to the array, which results in selective extension of the unblocked R2 primer (i.e. the R1 primer is not extended). Then in the third step of the first cycle, the array can be exposed to a treatment that selectively deblocks the R1 primer, for example, by cleavage of block1 (i.e. block2 is not cleaved). In the fourth step of the first cycle, a nucleotide having block1 and label1 is delivered to the array, which results in selective extension of the unblocked R1 primer (i.e. the R2 primer is not extended). The array can then be observed using a detection device such that the two labels can be distinguished at each site. As exemplified in FIG. 1, cycles of delivering nucleotides that are blocked and labeled, cleaving blocking groups and labels and detection can be repeated cyclically.

As exemplified above and in FIG. 1, the nucleotide analogs that are used to extend the primers can include reversible blocking moieties that are selectively cleavable to provide orthogonal control through multiple cycles of a sequencing by synthesis process. Thus, the nucleotide analogs can be provided in two sets: a first set having a first reversible blocking moiety (e.g. the same as the reversible blocking moiety on the first primer, block1) and a second set having a second reversible blocking moiety (e.g. block2). In some embodiments, the nucleotide analogs in the first set can have labels that are distinguishable from the labels on the nucleotide analogs in the second set (e.g. a first set is indicated at label1 and a second set is indicated as label2 in FIG. 1). The resulting orthogonality in biochemical reactivity and label management allows the two primer extension events to be distinguished from each other at each site of an array. Thus, the two target sequences can be distinguishably detected.

It will be understood that other methods can also benefit from orthogonal manipulation and detection as set forth in further detail below. Thus, the compositions, apparatus and methods set forth herein need not be limited to sequencing applications.

Orthogonality can be exploited to increase the density of information acquisition by 2-fold or more. For example, greater than 2-fold increase in information density can be obtained by using greater than two orthogonal reagent sets. As an example, 3 reagent sets can be used including 3 different deblocking treatments that are each selective for the primers and/or nucleotide analogs in one of the reagent sets.

As demonstrated above and as will be set forth in further detail below, the present disclosure provides the advantage of super-resolution imaging of an array, whereby the number of simultaneously resolvable target sequences at a given site is greater than one. Super-resolution imaging can provide the benefit of simultaneously distinguishing a number of different target nucleic acids that is larger than the number of sites on the array. Similarly, super-resolution is provided in that two different target sequences can be distinguished on a solid phase substrate using a detector that has a resolution that is lower than the spatial resolution that would otherwise be required to distinguish the two target sequences on the substrate.

In particular embodiments, this disclosure provides reagent and hardware configurations for efficient nucleic acid detection. An exemplary configuration uses fewer labels than the number of nucleotide analog species that is to be distinguished in a primer extension step. For example, four species of nucleotide analog can be distinguished based on detection of a single label species. As set forth in further detail below, this can be achieved by using a first set of nucleotide analogs including the following four species: (1) a species having a first label, (2) a species having a ligand, (3) a species having a cleavable linkage to the first label, and (4) a species lacking any label or ligand used in a subsequent step, wherein all four species have a blocking moiety that is selectively deblocked by a first treatment. An orthogonal set of nucleotide analogs can include the following four species (5) a species having a second label, (6) a species having a mixture of the first and second labels, (7) a species having a cleavable linkage to the second label, and (8) a species lacking any label or ligand used in a subsequent step wherein all four species have a blocking moiety that is selectively deblocked by a second treatment. Specifically, the first treatment does not cause substantial deblocking of the first set of nucleotide analogs and the second treatment does not cause substantial deblocking of the orthogonal set of nucleotide analogs.

The species within each set above can be distinguished from each other based on a proper accounting of what labels appear or disappear after specific fluidic steps and the two orthogonal sets of nucleotide analogs can be distinguished based on the two different labels. More specifically, species (1) and (5) can be distinguished from each other based on different labels and from all other species due to their appearance after an initial labeling step and their resistance to respective cleaving agent; species (2) can be distinguished based on appearance of label after incubation with a labeled receptor; species (3) and (7) can be distinguished from each other based on the different labels and are distinguished from all other species based upon initial appearance of the label and then disappearance after treatment with a respective cleavage reagent; species (6) can be distinguished from all other species based on the presence of both labels at an intensity that is half the intensity for fully labeled species; and species (4) and (8) can be distinguished based on inference from a lack of any other species in the respective sets having been detected. Many other configurations are possible to alter the number of labels, number of fluidic manipulations during a detection phase and/or the complexity of the detection device to distinguish a certain number of labels. As such, the configuration can be tailored to suit a particular approach or application.

Terms used herein will be understood to take on their ordinary meaning unless specified otherwise. Examples of several terms used herein and their definitions are set forth below.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from another amplicon. A subsequent amplicon can have a sequence that is substantially complementary to the target nucleic acid or substantially identical to the target nucleic acid.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). Alternatively a site can include a mixture of target nucleic acid sequences, for example, such that individual molecules contain two or more different molecules each or such that two or more molecules each contain a single target sequence of the mixture. The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions. A nucleic acid can be attached to a solid support via a gel coating on the solid support.

As used herein, the term "blocking moiety," when used in reference to a nucleotide analog, means a part of the nucleotide analog that inhibits or prevents the nucleotide analog from forming a covalent linkage to a second nucleotide analog. For example, in the case of nucleotide analogs having a pentose moiety, a blocking moiety can prevent formation of a phosphodiester bond between the 3' oxygen of the nucleotide analog and the 5' phosphate of the second nucleotide analog. The blocking moiety can be part of a nucleotide analog that is a monomer unit present in a nucleic acid polymer or the blocking moiety can be a part of a free nucleotide analog (e.g. a nucleotide triphosphate). The blocking moiety that is part of a nucleotide analog can be reversible, such that the blocking moiety can be removed or modified to render the nucleotide analog capable of forming a covalent linkage to a second nucleotide analog. Particularly useful reversible blocking moieties are phosphates, phosphoesters, alkyl azides, acetals, esters, ethers or the like. Further examples of reversible blocking moieties that can be used are set forth below and in references incorporated by reference herein as set forth below. In particular embodiments, a blocking moiety, such as a reversible blocking moiety, can be attached to the 3' position or 2' position of a pentose moiety of a nucleotide analog.

As used herein, the term "cluster," when used in reference to nucleic acids, refers to a population of the nucleic acids that is attached to a solid support to form a feature or site. The nucleic acids are generally of a single species, thereby forming a homogenous cluster. However, in some embodiments the nucleic acids can be heterogeneous, such that individual molecules having different sequences are present at the site or feature. The nucleic acids are generally covalently attached to the solid support, for example, via their 5' ends, but in some cases other attachment means are possible. The nucleic acids in a cluster can be single stranded or double stranded. In some but not all embodiments, clusters are made by a solid-phase amplification method known as bridge amplification. Exemplary configurations for clusters and methods for their production are set forth, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

As used herein, the term "deblocking agent" means a catalyst, enzyme, reagent or other substance that is capable of modifying or removing a blocking moiety. In particular embodiments, a deblocking agent can have specificity for a particular blocking moiety. As such the deblocking agent may selectively remove a particular blocking moiety from a nucleotide analog compared to another blocking moiety. Exemplary deblocking agents include, but are not limited to, an enzyme, such as a phosphoesterase, esterase, alkyl transferase or methyl transferase; or a chemical reagent such as a phosphine, proton, or chemical catalyst, such as palladium catalyst, or the like. Further examples of deblocking agents are set forth in further detail below.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different from each other while also having a universal sequence region that is the same for both. Generally, when two species are referred to herein as being "different," one of the species will have a structural property that is not the same as the structural properties of the second species. For example, two different polymeric species (such as two proteins) can have different sequences of monomeric subunits (such as different sequences of amino acids for two different proteins).

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art. The term "target," when used in reference to a nucleic acid, is intended as a semantic identifier for the nucleic acid in the context of a method or composition set forth herein and does not necessarily limit the structure or function of the nucleic acid beyond what is otherwise explicitly indicated.

As used herein, the term "nucleic acid template" refers to a nucleic acid or portion thereof that is capable of use as a guide for polymerase catalyzed replication. A nucleic acid molecule can include multiple templates along its length or, alternatively, only a single template per molecule may be used in a particular embodiment herein. A nucleic acid template can also function as a guide for ligase-catalyzed primer extension.

As used herein, the term "nucleotide" or "nucleotide analog" is intended to include natural nucleotides, non-natural nucleotides, ribonucleotides, deoxyribonucleotides, dideoxyribonucleotides and other molecules known as nucleotides. For example, the terms are used herein to generally refer to a nucleoside moiety (whether ribose, deoxyribose, or analog thereof) including a base moiety and optionally attached to one or more phosphate moieties. The term can be used to refer to a monomer unit that is present in a polymer, for example, to identify a subunit present in a DNA or RNA strand. The term can also be used to refer to a monomeric molecule that is not necessarily present in a polymer, for example, a molecule that is capable of being incorporated into a polynucleotide in a template dependent manner by a polymerase.

Exemplary nucleotide analogs include, but are not limited to, ribonucleotide monophosphate (sometimes referred to as a ribonucleoside monophosphate), ribonucleotide diphosphate (sometimes referred to as a ribonucleoside diphosphate), ribonucleotide triphosphate (sometimes referred to as a ribonucleoside triphosphate), deoxynucleotide monophosphate (sometimes referred to as a deoxynucleoside monophosphate), deoxynucleotide diphosphate (sometimes referred to as a deoxynucleoside diphosphate) and deoxynucleotide triphosphate (sometimes referred to as a deoxynucleoside triphosphate). For clarity when wishing to distinguish RNA components from DNA components, the term "ribonucleotide" can be used to specify RNA nucleotides, such as ribouridine triphosphate, riboguanidine triphosphate, ribocytidine triphosphate or riboadenosine triphosphate; and the term "deoxynucleotide" can be used to specify DNA nucleotides, such as deoxythymidine triphosphate, deoxyguanidine triphosphate, deoxycytidine triphosphate and deoxyadenosine triphosphate. In particular embodiments, the nucleotides are 'extendable', for example, lacking an extension blocking moiety at the 3' hydroxyl or at any other position on the nucleotide. In other embodiments, the nucleotides are 'blocked,' having a moiety that prevents the 3' position from participating in extension by addition of another nucleotide or oligonucleotide.

As used herein, the term "pitch" refers to the center to center distance for two sites in an array. A pattern of sites can be regular such that the coefficient of variation around the average pitch is small or the pattern can be non-regular in which case the coefficient of variation can be relatively large. In either case, the average pitch can be, for example, at least 10 nm, 0.1 µm, 0.5 µm, 1 µm, 5 µm, 10 µm, 100 µm or more. Alternatively or additionally, the average pitch can be, for example, at most 100 µm, 10 µm, 5 µm, 1 µm, 0.5 µm 0.1 µm or less. Of course, the average pitch for a particular pattern of sites can be between one of the lower values and one of the upper values selected from the ranges above.

As used herein, the term "primer" means a nucleic acid having a sequence that binds to a primer binding site at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof.

As used herein, the term "primer extension product" means a primer that has been modified by addition of at least one nucleotide analog. For example, a primer can be modified by addition of one or more nucleotide analogs to its 3' end (e.g. via polymerase catalysis), thereby forming a primer extension product. A primer extension product can alternatively be produced by ligation of an oligonucleotide to the 3' or 5' end of a primer. In this case, the primer extension product is extended by a length equivalent to the length of the oligonucleotide. A primer extension product can be at least 1, 2, 5, 10, 500, 1000 or more nucleotides longer than the primer. Alternatively or additionally, a primer extension product can be no more than 1, 2, 5, 10, 500, or 1000 nucleotides longer than the primer. For example, use of a blocked nucleotide analog provides for an extension product that is at least 1 nucleotide longer than the primer and also no more than 1 nucleotide longer than the primer.

As used herein, reference to "selectively" manipulating (or "selective" manipulation of) a first thing compared to second thing is intended to mean that the manipulation has a greater effect on the first thing compared to the effect on the second thing. The manipulation need not have any effect on the second thing. The manipulation can have an effect on the first thing that is at least 1%, 5%, 10%, 25%, 50%, 75%, 90%, 95%, or 99% greater than the effect on the second thing. The manipulation can have an effect on the first thing that is at least 2 fold, 3 fold, 4 fold, 5 fold, 10 fold, 100 fold, $1\times10^3$ fold, $1\times10^4$ fold or $1\times10^6$ fold higher than the effect on the second thing. The manipulation can include, for example, modifying, contacting, treating, changing, cleaving (e.g. of a chemical bond), photo-chemically cleaving (e.g. of a chemical bond), forming (e.g. of a chemical bond), photo-chemically forming (e.g. of a chemical bond), covalently modifying, non-covalently modifying, destroying, photo-ablating, removing, synthesizing, polymerizing, photo-polymerizing, amplifying (e.g. of a nucleic acid), copying (e.g. of a nucleic acid), extending (e.g. of a nucleic acid), ligating (e.g. of a nucleic acid), or other manipulation set forth herein or otherwise known in the art.

As used herein, the term "sequence," when used in reference to a nucleic acid, refers to the order of nucleotides (or bases) in the nucleic acids. In cases where, different species of nucleotides are present in the nucleic acid, the sequence includes an identification of the species of nucleotide (or base) at respective positions in the nucleic acid. A sequence is a property of all or part of a nucleic acid molecule. The term can be used similarly to describe the order and positional identity of monomeric units in other polymers such as amino acid monomeric units of protein polymers.

As used herein, the term "site" means a location in an array where at least one analyte molecule is present. A site can contain only a single analyte molecule or it can contain a population of several analyte molecules of the same species. In some embodiments, a site can include multiple different analyte molecule species, each species being present in one or more copies. Sites of an array are typically discrete. The discrete sites can be contiguous or they can have spaces between each other.

As used herein, the term "species" or "type" is used to identify molecules that share the same chemical structure.

For example, a mixture of nucleotide analogs can include several dCTP molecules. The dCTP molecules will be understood to be the same species, or type, as each other, but a different species, or types, compared to dATP, dGTP, dTTP etc. Similarly, individual DNA molecules that have the same sequence of nucleotides are the same species, or type, whereas DNA molecules with different sequences are different species or types. As another example, a DNA polymerase is a different polymerase species, or type, compared to an RNA polymerase (even if the two polymerases are derived from the same organism).

As used herein, the term "universal sequence" refers to a sequence that is common to two or more nucleic acid molecules, even where the molecules also have other regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication or amplification of multiple different nucleic acids using a population of universal primers that are complementary to the universal sequence. Thus a universal capture nucleic acid or a universal primer includes a sequence that can hybridize specifically to a universal sequence. Target nucleic acid molecules may be modified to attach universal adapters, for example, at one or both ends of the different target sequences.

The embodiments set forth below and recited in the claims can be understood in view of the above definitions.

The present disclosure provides a method for sequencing nucleic acid templates. The method can include steps of (a) providing an array of sites, wherein each site comprises a mixture of at least two different nucleic acid templates; (b) extending primers hybridized to the different nucleic acid templates at each of the sites with different nucleotide analogs having different reversible blocking moieties, respectively, thereby producing different primer extension products at each site; (c) detecting the different primer extension products to distinguish the different nucleotide analogs at each site; (d) removing the different reversible blocking moieties from the primer extension products at each of the sites using a first treatment that is selective for a first of the different reversible blocking moieties and a second treatment that is selective for a second of the different reversible blocking moieties; and (e) repeating (b) through (d) to determine the sequence of different nucleotide analogs added to each of the different extension products at each of the sites.

As set forth above, a method of the present disclosure can include a step of providing first and second nucleic acid templates, wherein the sequences for the two templates are different. The two template sequences can be portions of a single nucleic acid molecule or, alternatively, the two template sequences can be located on separate molecules. As set forth in further detail elsewhere herein, the two template sequences may be in a proximity that is too close to spatially resolve with the detection system used. Nevertheless, the orthogonal detection methods of the present disclosure allow these template sequences to be distinguished. The orthogonal detection scheme is exemplified for two template sequences, but can be used with two or more template sequences. Accordingly, a system or method set forth herein can include at least 2, 3, 4, 5, 10 or more template sequences that are in close proximity, for example on a single nucleic acid molecule, at a single site of an array, or otherwise in a proximity that is too close to spatially resolve with the detection system used.

Target nucleic acids used herein can be composed of DNA, RNA or analogs thereof. The source of the target nucleic acids can be genomic DNA, messenger RNA, or other nucleic acids from native sources. In some cases the target nucleic acids that are derived from such sources can be amplified prior to use in a method or composition herein.

Exemplary biological samples from which target nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Target nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Target nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

In particular embodiments, a nucleic acid sample can be modified or prepared for use in one or more of the methods set forth herein. In some cases it is desired to add one or more primer binding sites to a nucleic acid. Known molecular biological techniques can be used to introduce primer binding sites upstream of respective template sequences, for example, via insertion of an adapter having the primer binding site, mutation to create the primer binding site, ligation of an adapter having the primer binding site etc. Useful methods are described in Sambrook et al., supra and Ausubel et al., supra. US Pat. App. Pub. No. 2015/0031560 A1 (which is incorporated herein by reference) provides an illustration of a tagmentation-based technique for introducing primer binding sites. Tagmentation is particularly useful for introducing one or more primer binding sites and can be carried out, for example, using techniques set forth in U.S. Pat. Nos. 6,294,385 and 8,383,345, and PCT Pub. No. WO 2012/106546, each of which is incorporated herein by reference. It will be understood that in some cases naturally occurring sequence regions that reside upstream of respective template sequences can be exploited as primer binding sites in a method set forth herein. Methods similar to those exemplified above for primer binding sites can be used to introduce other desired sequence elements such as promoter elements for RNA polymerase-based extension or tag sequences.

Universal priming sites are particularly useful for multiplex applications of the methods set forth herein. Universal priming sites provide a region of sequence that is common to two or more nucleic acid molecules where the molecules also have template or target regions with different sequences. A universal priming sequence present in different members of a collection of molecules can allow the replication, amplification or detection of multiple different sequences using a single universal primer species that is complementary to the universal priming sequence. Thus, a universal primer includes a sequence that can hybridize specifically to a universal priming sequence. Examples of methods of attaching universal sequences to a collection of target nucleic acids can be found in US Pat. App. Pub. No. 2007/0128624 A1, which is incorporated herein by reference.

In some embodiments, target nucleic acids can be obtained as fragments of one or more larger nucleic acids. Fragmentation can be carried out using any of a variety of techniques known in the art including, for example, nebulization, sonication, chemical cleavage, enzymatic cleavage, or physical shearing. Fragmentation may also result from use of a particular amplification technique that produces amplicons by copying only a portion of a larger nucleic acid. For example, PCR amplification produces fragments having a size defined by the length of the fragment between the flanking primers used for amplification.

A population of target nucleic acids, or amplicons thereof, can have an average strand length that is desired or appropriate for a particular application of the methods or compositions set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for a population of target nucleic acids, or amplicons thereof, can be in a range between a maximum and minimum value set forth above. It will be understood that amplicons generated at an amplification site (or otherwise made or used herein) can have an average strand length that is in a range between an upper and lower limit selected from those exemplified above.

In some cases a population of target nucleic acids can be produced or otherwise configured to have a maximum length for its members. For example, the maximum length for the members that are made or used as set forth herein can be less than about 100,000 nucleotides, 50,000 nucleotides, 10,000 nucleotides, 5,000 nucleotides, 1,000 nucleotides, 500 nucleotides, 100 nucleotides or 50 nucleotides. Alternatively or additionally, a population of target nucleic acids, or amplicons thereof, can be produced under conditions or otherwise configured to have a minimum length for its members. For example, the minimum length for the members that are used in one or more steps of a method set forth herein or that are present in a particular composition can be more than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The maximum and minimum strand length for target nucleic acids in a population can be in a range between a maximum and minimum value set forth above. It will be understood that amplicons generated at a site of an array (or otherwise made or used herein) can have maximum and/or minimum strand lengths in a range between the upper and lower limits exemplified above.

Any of a variety of known amplification techniques can be used to increase the amount of template sequences present for use in a method set forth herein. Exemplary techniques include, but are not limited to, polymerase chain reaction (PCR), rolling circle amplification (RCA), multiple displacement amplification (MDA), or random prime amplification (RPA) of nucleic acid molecules having template sequences. It will be understood that amplification of target nucleic acids prior to use in a method or composition set forth herein is optional. As such, target nucleic acids will not be amplified prior to use in some embodiments of the methods and compositions set forth herein. Target nucleic acids can optionally be derived from synthetic libraries. Synthetic nucleic acids can have native DNA or RNA compositions or can be analogs thereof. Solid-phase amplification methods can also be used, including for example, cluster amplification, bridge amplification or other methods set forth below in the context of array-based methods.

A nucleic acid used in a method set forth herein can be solution phase or solid-phase. The nucleic acid when in solution phase is generally soluble, but can also be in a suspended form that is capable of being precipitated, as is the case for some large nucleic acid species such as chromosomes or nucleic acid nanoballs (see, for example, US Pat. App. Pub. No. 2007/0099208 A1, which is incorporated herein by reference). A nucleic acid that is solid-phase can occur in or on a solid-phase support. Exemplary solid-phase supports include those made from glass, nitrocellulose, silica, metal, plastic and other materials set forth elsewhere herein, for example, with regard to array formats and flow cells. Similarly, a nucleic acid can occur in or on a semisolid support such as a gel. Exemplary gels that are useful include, but are not limited to, those having a colloidal structure, such as agarose; polymer mesh structure, such as gelatin; or cross-linked polymer structure, such as polyacrylamide. Hydrogels are particularly useful such as those set forth in US Pat. App. Pub. No. 2011/0059865 A1 and U.S. Pat. No. 9,012,022, each of which is incorporated herein by reference.

Attachment of a nucleic acid to a support, whether rigid or semi-rigid, can occur via covalent or non-covalent linkage(s). Exemplary linkages are set forth in U.S. Pat. Nos. 6,737,236; 7,259,258; 7,375,234 and 7,427,678; and US Pat. App. Pub. No. 2011/0059865 A1, each of which is incorporated herein by reference. In some embodiments, a nucleic acid or other reaction component can be attached to a gel or other semisolid support that is in turn attached or adhered to a solid-phase support. In such embodiments, the nucleic acid or other reaction component will be understood to be solid-phase.

A multiplex reaction can utilize a solid-phase support (a.k.a. a solid support). A solid-phase support can be useful for separating individual reactions such that each can be interrogated separately or individually. For example, several different nucleic acids in a mixture can be attached to the solid-phase support. The nucleic acids can be attached to the solid-phase support in an array format.

In some embodiments, an array of sites is provided, wherein each site includes a first nucleic acid template and a second nucleic acid template and wherein the first nucleic acid template has a sequence that is different from the sequence of the second nucleic acid template. There can be greater than two different templates per site in some embodiments. Exemplary array materials and manufacturing methods that can be modified for use herein include, without limitation, a BeadChip Array available from Illumina®, Inc. (San Diego, Calif.) or arrays such as those described in U.S. Pat. Nos. 6,266,459, 6,355,431, 6,770,441, 6,859,570 or 7,622,294; or PCT Pub. No. WO 00/63437, each of which is incorporated herein by reference. Further examples of commercially available arrays that can be used include, for example, an Affymetrix® GeneChip® array or other array synthesized in accordance with techniques sometimes referred to as VLSIPS™ (Very Large Scale Immobilized Polymer Synthesis) technologies. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays that can be used, for example, by modifying the sites to include multiple different template nucleic acid sequences, include those that are used in nucleic acid sequencing applications. For example, arrays having amplicons of genomic fragments (often referred to as clusters) are particularly useful such as those described in Bentley et al., *Nature* 456:53-59 (2008), PCT Pub. Nos. WO 04/018497, WO 91/06678, or WO 07/123744; U.S. Pat. Nos. 7,057,026, 7,329,492, 7,211,414, 7,315,019, or 7,405,281; or US Pat. App. Pub. No. 2008/0108082 A1, each of which is incorporated herein by reference.

Nucleic acid clusters can be created by solid-phase amplification methods. For example, a nucleic acid having one or more template sequences to be detected can be attached to a surface and amplified using bridge amplification. Useful bridge amplification methods are described, for example, in U.S. Pat. No. 5,641,658 or 7,115,400; or U.S. Pat. App. Pub. Nos. 2002/0055100 A1, 2004/0096853 A1, 2004/0002090 A1, 2007/0128624 A1 or 2008/0009420 A1, each of which is incorporated herein by reference. Another useful method for amplifying nucleic acids on a surface is rolling circle amplification (RCA), for example, as described in Lizardi et al., *Nat. Genet.* 19:225-232 (1998) and US Pat. App. Pub. No. 2007/0099208 A1, each of which is incorporated herein by reference. Another type of array that is useful is an array of particles produced from an emulsion PCR amplification technique. Examples are described in Dressman et al., *Proc. Natl. Acad. Sci. USA* 100:8817-8822 (2003), PCT app. Pub. No. WO 05/010145, or US Pat App. Pub. No. 2005/0130173 A1 or 2005/0064460 A1, each of which is incorporated herein by reference. Although the above arrays have been described in the context of sequencing applications, it will be understood that the arrays can be used in other embodiments including, for example, those that use a non-cyclic primer extension technique.

Detection can be carried out at ensemble or single molecule levels on an array. Ensemble level detection is detection that occurs in a way that several copies of a single template sequence (e.g. multiple amplicons of a template) are detected at each individual site and individual copies at the site are not distinguished from each other. Thus, ensemble detection provides an average signal from many copies of a particular template sequence at the site. For example, the site can contain at least 10, 100, 1000 or more copies of a particular template sequence. Of course, a site can contain multiple different template sequences each of which is present as an ensemble. Alternatively, detection at a single molecule level includes detection that occurs in a way that individual template sequences are individually resolved on the array, each at a different site. Thus, single molecule detection provides a signal from an individual molecule that is distinguished from one or more signals that may arise from a population of molecules within which the individual molecule is present. Of course, even in a single molecule array, a site can contain several different template sequences (e.g. two or more template sequence regions located along a single nucleic acid molecule).

An array of sites can appear as a grid of spots or patches. The sites can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful.

The size of the sites and/or spacing between the sites in an array can vary to achieve high density, medium density or lower density. High density arrays are characterized as having sites with a pitch that is less than about 15 µm. Medium density arrays have sites with a pitch that is about 15 to 30 µm, while low density arrays have a pitch that is greater than 30 µm. An array useful in some embodiments can have sites with a pitch that is less than 100 µm, 50 µm, 10 µm, 5 µm, 1 µm, or 0.5 µm. An embodiment of the methods set forth herein can be used to image an array at a resolution sufficient to distinguish sites at the above densities or density ranges. However, the detecting step will typically use a detector having a spatial resolution that is too low to resolve points at distance equivalent to the spacing between a first template (or first primer extension product hybridized thereto) and a second template (or second primer extension product hybridized thereto) at an individual site. In particular embodiments, sites of an array can each have an area that is larger than about 100 nm$^2$, 250 nm$^2$, 500 nm$^2$, 1 µm$^2$, 2.5 µm$^2$, 5 µm$^2$, 10 µm$^2$, 100 µm$^2$, or 500 µm$^2$. Alternatively or additionally, sites of an array can each have an area that is smaller than about 1 mm$^2$, 500 µm$^2$, 100 µm$^2$, 25 µm$^2$, 10 µm$^2$, 5 µm$^2$, 1 µm$^2$, 500 nm$^2$, or 100 nm$^2$. Indeed, a site can have a size that is in a range between an upper and lower limit selected from those exemplified above.

The methods set forth herein can use arrays having sites at any of a variety of densities including, for example, at least about 10 sites/cm$^2$, 100 sites/cm$^2$, 500 sites/cm$^2$, 1,000 sites/cm$^2$, 5,000 sites/cm$^2$, 10,000 sites/cm$^2$, 50,000 sites/cm$^2$, 100,000 sites/cm$^2$, 1,000,000 sites/cm$^2$, 5,000,000 sites/cm$^2$, or higher.

Generally, an array will have sites with different nucleic acid sequence content. Accordingly, each of the sites in an array can contain a nucleic acid sequence that is unique compared to the nucleic acid sequences at the other sites in the array. However, in some cases an array can have redundancy such that two or more sites have the same nucleic acid content.

It will be understood that the steps of the methods set forth herein can be carried out in a manner to expose an entire site or a plurality of sites of an array with the treatment. For example, a step that involves extension of a primer can be carried out by delivering primer extension reagents to an array such that multiple nucleic acids (e.g. different nucleic acids in a mixture) at each of one or more sites of the array are contacted with the primer extension reagents. Similarly a step of deblocking a blocked primer extension product can be carried out by exposing an array with a deblocking treatment such that multiple nucleic acids (e.g. different nucleic acids in a mixture) at each of one or more sites of the array are contacted with the treatment.

At any given point in a sequencing-by-synthesis, or other primer extension reaction, the species of nucleotide that is present in a first template at the position that complements the site of primer extension can be the same as the species of nucleotide that is present in a second template at the position that complements the site of primer extension. In other words, the first nucleic acid template at a particular site of an array can include at least one base moiety that is the same species as a base moiety in the second nucleic acid template at that particular site, and a complementary nucleotide analog can be added to each of the primers at the positions in the templates where those base moieties reside. This can be the case whether or not the template sequences to which the primers are hybridized are the same or different. Techniques set forth in further detail below can be used to distinguish the two templates, for example, the use of different sets of nucleotide analogs having mutually distinguishable labels.

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. A particularly useful function of a polymerase is to catalyze the polymerization of a nucleic acid strand using an existing nucleic acid as a template. Other functions that are useful are described elsewhere herein. Examples of useful polymerases include DNA polymerases, reverse transcriptases and RNA polymerases.

A polymerase having an intrinsic 3' to 5' proofreading exonuclease activity can be useful for some embodiments. Polymerases that substantially lack 3' to 5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3' to 5' proofreading exonuclease activity.

Depending on the embodiment that is to be used, a polymerase can be either thermophilic or heat inactivatable. Thermophilic polymerases are typically useful for high temperature conditions or in thermocycling conditions such as those employed for polymerase chain reaction (PCR) techniques. Examples of thermophilic polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Examples are DNA polymerases from phage. It will be understood that polymerases from any of a variety of sources can be modified to increase or decrease their tolerance to high temperature conditions. Particularly useful polymerases for incorporating nucleotide analogs having labels and/or reversible terminating moieties are described in US 2006/0281109 A1, which is incorporated herein by reference.

In particular embodiments of the methods and compositions set forth herein, only a single species of polymerase will be used. In such examples, each site of an array will interact with only one species of polymerase at a given time even though multiple polymerases may be present at the site and bound to multiple primed-templates at each site. For example, all sites of an array may interact with a particular species of DNA polymerase and other polymerases (such as RNA polymerases) will be absent from the array.

Another extension technique that can be modified for use in a method or composition set forth herein is a ligase based system that is selective for incorporation of oligonucleotides instead of monomeric nucleotides that are incorporated by the polymerase-based extension systems described above. A DNA ligase reagent system that uses a first set of oligonucleotides having a reversible blocking moiety that is selectively deblocked by a first deblocking treatment is orthogonal with a reagent system that uses a second set of oligonucleotides having a reversible blocking moiety that is selectively deblocked by a second deblocking treatment. Deblocking of primers extended with reversibly blocked oligonucleotides can be carried out in an orthogonal fashion much like exemplified herein for deblocking of primers extended with reversibly blocked nucleotide analogs. Extension by ligation can be carried out in a sequencing application using a population of partially random probe oligonucleotides having a one- or two-base encoding scheme. Ligation based extension techniques that can be modified for use herein, such as in a sequencing context, are set forth in McKernan et al., *Genome Research* 19 (9): 1527-41 (2009); Shendure et al., *Science* 309:1728-1732 (2005); or U.S. Pat. No. 5,599,675 or 5,750,341, each of which is incorporated herein by reference.

A nucleic acid extension reaction, or other cyclic reaction, that is carried out using methods set forth herein can proceed for one or more cycles. In particular embodiments, a multicycle reaction can include at least 2 cycles, 5 cycles, 10 cycles, 50 cycles, 100 cycles, 500 cycles, 1,000 cycles, 5,000 cycles, 10,000 cycles or more. Alternatively or additionally, a reaction can have an upper limit whereby no more than 1 cycle, 2 cycles, 5 cycles, 10 cycles, 50 cycles, 100 cycles, 500 cycles, 1,000 cycles, 5,000 cycles, or 10,000 cycles occur. In some embodiments, each cycle will result in the incorporation of a single nucleotide analog into an extended primer. In this case, the minimum or maximum number of cycles exemplified above can be understood to exemplify the minimum or maximum number of nucleotides incorporated into an extension product in a polymerase catalyzed reaction.

Some embodiments can use non-cyclic extension reactions such as single base extension (SBE) or allele specific primer extension (ASPE) reactions. Reversible terminator moieties can be used to achieve orthogonal extension of two different primers in a non-cyclic extension format. Since a deblocking step is not necessary for continuation of these non-cyclic reactions (i.e. once the primers have been extended), the nucleotide analogs used in the extension step can instead be non-reversibly terminated. For example, dideoxynucleotides can be used. Exemplary reagents and related techniques for SBE, ASPE and other useful non-cyclic extension techniques are described, for example, in U.S. Pat. No. 7,670,810 or U.S. Pat. App. Pub. Nos. 2003/0108867; 2003/0108900; 2003/0170684; 2003/0207295; or 2005/0181394, each of which is incorporated herein by reference. An example of a commercially available product that uses a non-cyclic extension technique and that can be modified to increase information content via the orthogonal detection methods set forth herein is the Infinium® genotyping product available from Illumina, Inc. (San Diego, Calif.).

Cyclic and non-cyclic reactions alike can include steps where reaction components are separated from each other or removed from the reaction environment. One or more reaction components can be separated, for example, by separation of solid-phase components from liquid-phase components. Wash steps can optionally be included in order to more completely remove unwanted liquid-phase component(s) from solid-phase component(s). A particularly useful reaction vessel for such separations is a flow cell such as those commonly used in cyclical sequencing procedures. Exemplary flow cells, methods for their manufacture and methods for their use are described in US Pat. App. Publ.

Nos. 2010/0111768 A1 or 2012/0270305 A1; or PCT App. Pub. No. WO 05/065814, each of which is incorporated herein by reference. Whether or not solid-phase separation methods are used, reaction components can be removed by any of a variety of other techniques known in the art including, liquid-liquid extraction, solid-phase extraction, chromatography, filtration, centrifugation or the like.

Reversible terminator moieties provide a convenient way to control an extension reaction to add only a single nucleotide to a primer until a subsequent deblocking step is carried out. As set forth herein, the use of orthogonal blocking moieties and deblocking treatments provide super resolution detection, whereby a greater complexity of templates can be monitored and detected than would otherwise be allowed using a non-orthogonal technique. Examples of reversible blocking moieties and their deblocking conditions include, but are not limited to, moieties that can be photocleavably removed from the 3' position such as o-nitrobenzylethers and alkyl o-nitrobenzyl carbonate; ester moieties that can be removed by base hydrolysis; allyl-moieties that can be removed with NaI, chlorotrimethylsilane and $Na_2S_2O_3$ or with Hg(II) in acetone/water; -azidomethyl ($-CH_2-N_3$) which can be cleaved with phosphines, such as tris(2-carboxyethyl)phosphine (TCEP) or tri(hydroxypropyl)phosphine (THP); acetals, such as tert-butoxy-ethoxy which can be cleaved with acidic conditions; MOM ($-CH_2OCH_3$) moieties that can be cleaved with $LiBF_4$ and $CH_3CN/H_2O$; 2,4-dinitrobenzene sulfenyl which can be cleaved with nucleophiles such as thiophenol and thiosulfate; tetrahydrofuranyl ether which can be cleaved with Ag(I) or Hg(II); and 3' phosphate which can be cleaved by phosphatase enzymes (e.g. polynucleotide kinase). Other useful reversible moieties include ethers, $-F$, $-NH_2$, $-OCH_3$, $-N_3$, $-NHCOCH_3$, and 2-nitrobenzene carbonate. Useful deblocking treatments include irradiation with light (e.g. to induce photocleavage), heating, exposure to chemical reactants, exposure to catalysts, exposure to electrical current (e.g. to induce electrolysis) or the like.

Particular embodiments of the methods herein can employ reversibly blocked primers and reversibly blocked nucleotide analogs, for example, in a multicycle process such as sequencing-by-synthesis. As exemplified previously herein, a particular reversibly blocked primer and a particular set of reversibly blocked nucleotide analogs can be susceptible to the same deblocking conditions. This can be due to the same species of reversible blocking moiety being present on the primer and on the nucleotide analogs in the set. However, it is also possible to use different blocking moieties that are nonetheless susceptible to the same deblocking treatment.

A reversible blocking moiety can be attached to the 3' nucleotide of a primer. Generally, the reversible blocking moiety is attached at the 3' positon of the ribose sugar moiety. However, a blocking moiety can be attached to alternative positions instead, including for example, at the 2' position of the ribose or on the base moiety. A blocking moiety can also be attached at the 5' end of a primer, for example, at the 5' position of the ribose of the terminal nucleotide or at the 5' phosphate moiety. Primers that are blocked at the 5' end can be useful for embodiments that employ ligation techniques.

The 3' or 5' end of a primer can be attached to a label moiety such as an optical label. The label can be present whether or not a reversible blocking moiety is also present on the primer. In some cases, a particular moiety can function as both a label and as a reversible block to primer extension.

The same attachment points for a label and/or reversible blocking moiety that are exemplified above for primers, can be useful for individual nucleotides.

Further exemplary guidance regarding blocking moieties and deblocking treatments are described, for example, in Bentley et al., *Nature* 456:53-59 (2008), PCT App. Pub. Nos. WO 04/018497, WO 91/06678 or WO 07/123744; U.S. Pat. Nos. 7,057,026, 7,329,492, 7,211,414, 7,315,019, 8,088,575 or 7,405,281; or US Pat. App. Pub. No. 2008/0108082 A1, each of which is incorporated herein by reference.

Orthogonal manipulation and detection in accordance with the present disclosure does not require that two template sequences differ at every position along their length. Rather, the same base moiety can be present at positions that are detected on a first template and second template, respectively. The two positions can be distinguished based on the distinguishable characteristics of the labels present in the orthogonal reagent systems and the specificity of the reagent systems for extending the appropriately deblocked primer. This information can in turn be used to distinguishably detect the two different template sequences, even if the two positions are detected simultaneously using a detector having a resolution that is too low to resolve points at distance equivalent to the spacing of the two template sequences.

Any of a variety of labels can be used. A label moiety that is particularly useful when used for detection of a nucleotide analog, can be any part of the nucleotide analog that provides a distinguishable characteristic when compared to other molecules present in its environment. The distinguishable characteristic can be, for example, an optical signal such as absorbance of radiation, fluorescence emission, luminescence emission, fluorescence lifetime, fluorescence polarization, or the like; binding affinity for a ligand or receptor; magnetic properties; electrical properties; charge; mass; radioactivity or the like. Exemplary label moieties include, without limitation, a fluorophore, luminophore, chromophore, radioactive isotope, mass label, charge label, spin label, receptor, ligand, or the like. The label moiety can be part of a nucleotide that is a monomer unit present in a nucleic acid polymer or the label moiety can be a part of a free nucleotide analog (e.g. a nucleotide triphosphate).

Fluorophores are particularly useful and include, for example, fluorescent nanocrystals; quantum dots, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue, Texas Red, Alexa dyes, SETA dyes, Atto dyes, phycoerythin, bodipy, and analogs thereof. Useful optical probes are described in Lakowicz, *Principles of Fluorescence Spectroscopy*, $3^{rd}$ Ed. Springer (2006); Haugland, *Handbook of Fluorescent Probes and Research Products* $9^{th}$ Ed., Molecular Probes, Inc, (2002); Shapiro, *Practical Flow Cytometry*, $4^{th}$ Ed., John Wiley & Sons (2003); PCT Pat. App. Pub. Nos. WO 98/59066 or WO 91/06678; or US Pat. App. Pub. No. 2010/0092957 A1, each of which is incorporated herein by reference.

Other labels, some of which are non-optical labels, can be used in various embodiments of the methods and compositions set forth herein. Examples include, without limitation, an isotopic label such as a naturally non-abundant radioactive or heavy isotope; magnetic substance; electron-rich material such as a metal; electrochemiluminescent label such as $Ru(bpy)^{32+}$; or moiety that can be detected based on a nuclear magnetic, paramagnetic, electrical, charge to mass, or thermal characteristic. Labels can also include magnetic particles or optically encoded nanoparticles. Such labels can be detected using appropriate methods known to those skilled in the art. For example, a charged label can be detected using an electrical detector such as those used in commercially available sequencing systems from Ion Torrent (Guilford, Conn., a Life Technologies subsidiary) or detection systems described in US Pat. App. Publ. Nos. 2009/0026082 A1; 2009/0127589 A1; 2010/0137143 A1; or 2010/0282617 A1, each of which is incorporated herein by reference. It will be understood that for some embodiments a nucleotide analog can be devoid of one or more of the labels set forth herein.

A label moiety can be attached to a nucleotide analog in a variety of ways. Exemplary attachments and label compositions that are useful for nucleotide analogs are set forth in Bentley et al., Nature 456:53-59 (2008), PCT App. Pub. Nos. WO 04/018497, WO 91/06678 or WO 07/123744; U.S. Pat. Nos. 7,057,026, 7,329,492, 7,211,414, 7,315,019, 8,088,575 or 7,405,281; or US Pat. App. Pub. No. 2008/0108082 A1, each of which is incorporated herein by reference.

A detection step of a method set forth herein, can be carried out in a method of the present disclosure using an apparatus suited to the particular label in use. For example, an optical detector such as a fluorescence detector, absorbance detector, luminescence detector or the like can be used to detect appropriate optical labels. Systems designed for array-based detection are particularly useful. For example, optical systems for use with the methods set forth herein may be constructed to include various components and assemblies as described in U.S. Pat. Nos. 8,241,573; 7,329,860 or 8,039,817; or US Pat. App. Pub. Nos. 2009/0272914 A1 or 2012/0270305 A1, each of which is incorporated herein by reference.

An orthogonal detection system, such as a system used for sequencing-by-synthesis, can use different labels to distinguish different nucleotides that are added to each primer. In one embodiment, each nucleotide species will have a unique optical label that produces a unique signal for distinguishing that nucleotide species. An example is an 8 dye approach. In this example, a first set of 4 different nucleotide analogs each has a different fluorescent dyes that distinguishes each of the 4 different nucleotide analogs from each other, wherein the 4 different nucleotides in the first set have blocking moieties that can be selectively deblocked by a first treatment. A second set of 4 different nucleotide analogs each has a different fluorescent dyes that distinguishes each of the 4 different nucleotide analogs from each other, wherein the 4 different nucleotides in the second set have blocking moieties that can be selectively deblocked by a second treatment. In this case the first treatment is selective for the blocking moieties in the first set of nucleotides, and the second treatment is selective for the blocking moieties in the second set of nucleotides. The two sets of dyes are unique such that the 8 dyes produce 8 distinguishable signals, respectively.

In embodiments where all of the nucleotide analogs are distinguishably labeled, such as the above-described 8 dye approach, a pair of template sequences can be contacted with all of the nucleotide analogs and then detection can be performed afterwards. Here the ability to distinguish all of the nucleotide analogs due to unique optical labels provides the benefit of relatively simple fluidic manipulations, whereby all of the nucleotide analogs can be delivered to the template sequences such that they are simultaneously present. In a relatively straightforward and preferred embodiment all 8 nucleotide analogs are delivered simultaneously; however, one or more subsets can be delivered sequentially if desired. Detection can occur during or after nucleotide analog delivery. This relatively simple fluidic process is accommodated by a relatively complex detection device having the ability to distinguish all of the different signals. For example, a fluorescence detection system able to distinguish 8 different fluorescent signals can be used for the 8 dye approach Those skilled in the art will know or be able to determine an appropriate fluorescent detection apparatus to achieve this sort of signal differentiation. For example, excitation and emission properties of the fluorescent labels can be appropriately matched with a combination of excitation wavelengths produced and emission wavelengths detected by a fluorometer. Exemplary guides for optics and labels useful for multiwavelength fluorescence detection are provided in Lakowicz, Principles of Fluorescence Spectroscopy, $3^{rd}$ Ed. Springer (2006); Haugland, Handbook of Fluorescent Probes and Research Products $9^{th}$ Ed., Molecular Probes, Inc, (2002); and Shapiro, Practical Flow Cytometry, $4^{th}$ Ed., John Wiley & Sons (2003), each of which is incorporated herein by reference.

The principles exemplified above for a system in which all of the nucleotides are distinguishably labeled, can be readily extended to an array format. An array having a sufficient number and variety of different template sequences will be expected to incorporate all of the labeled nucleotides when treated with primer extension reaction systems. More specifically, in an array-based approach, having a wide variety of nucleic acids across the array sites and having two different templates per site, all possible 2-dye dye combinations will be expected to occur on the array following a primer extension cycle in which all 8 nucleotides were delivered to the array. The sites can be spatially distinguished using optical devices known in the art, for example, those described in U.S. Pat. Nos. 8,241,573; 7,329,860 or 8,039,817; or US Pat. App. Pub. Nos. 2009/0272914 A1 or 2012/0270305 A1, each of which is incorporated herein by reference. Such detection systems can be readily modified to accommodate 8-color fluorescent detection as set forth above. A detection system that is modified in this way will be capable of multiplex orthogonal detection such that two different templates are distinguished (e.g. via sequencing) at multiple sites each having a different sequence composition.

In some embodiments, the number of different signals that are distinguished in a particular method is less than the number of different nucleotide analog species used in that method. For example, multiple different nucleotide analog species can have the same label and/or a subset of the nucleotide species can be unlabeled. An example of a configuration that uses the same label for multiple different nucleotide species is the case of an orthogonal primer extension method where a first set of 4 different nucleotide analogs share a first label in common and are susceptible to a first selective deblocking treatment, whereas a second set of 4 different nucleotide analogs share a second label in common and are susceptible to a second deblocking treatment. In this example the first label is optically distinguishable from the second label, the first treatment is selective for the first set of nucleotide analogs and the second treatment is selective for the second set of nucleotide analogs. In this configuration, the 4 different nucleotides in the first set can be distinguished from each other by sequential cycles of delivery and detection (i.e. a separate cycle for each of the different nucleotide analogs). So long as the first label and second label in this example are distinguishable, members of the tow sets of nucleotides can be delivered in pairs (1 each of a single nucleotide species from the first set and a single nucleotide species from the second set), in 4 cycles of delivery and detection. Thus, members of a first set of nucleotide analogs used in a primer extension reaction can include only one type of optical label that gets detected and a second set of nucleotide analogs, that is orthogonal to the first set can also include only one type of optical label that gets detected, wherein the label used in the first set is optically distinguishable from the label used in the second set.

Greyscaling allows use of multiple different nucleotide analog species that have the same label. Here different nucleotide analog species can be distinguished based on the intensity of label signal detected. For example, each species of nucleotide analog can be delivered as a uniquely proportioned mixture of that species in labeled and unlabeled form. Variation in the ratio of labeled:unlabeled nucleotide analog for each species will result in a uniquely greyscaled signal output for each mixture. By way of more specific example, a first nucleotide analog can be fully labeled (no mixing of labeled and unlabeled first nucleotide analog), a second nucleotide analog can be 75% labeled (a mix of 75% labeled and 25% unlabeled second nucleotide analog), a third nucleotide analog can be 50% labeled (a mix of 50% labeled and 50% unlabeled third nucleotide analog), and a fourth nucleotide analog can be 25% labeled (a mix of 25% labeled and 75% unlabeled fourth nucleotide analog). These 4 nucleotide analog species can be distinguished based on the resulting differences in signal intensity, whereby a population of appropriately deblocked primers (e.g. at an array site) will produce full signal due to incorporation of the first nucleotide analog; 75% signal due to incorporation of the second nucleotide analog, 50% signal due to incorporation of the third nucleotide analog and 25% signal due to incorporation of the fourth nucleotide analog.

In particular embodiments, at least one of the nucleotide analog species can be entirely unlabeled. Thus, in a case where optical labels are present on the other nucleotide analogs in a set of nucleotide analogs, there can also be a 'dark' nucleotide analog. Extension of a primer to incorporate a dark, or otherwise unlabeled, nucleotide analog can be determined by inference based on the absence of a label that would be expected if the other nucleotide analogs in the set were to have been incorporated by the extension reaction. Thus, in some embodiments only a subset of the nucleotide analogs used in a primer extension reaction set forth herein need to have a label.

Use of entirely unlabeled nucleotide analog species can be combined with greyscaling. For example, three of four different nucleotide analog species in a set (i.e. a set that can be deblocked by a common treatment) can have distinguishable nonzero amounts of a particular label (e.g. ratios of labeled and non-labeled nucleotide analogs in a mixture) and the fourth nucleotide analog species can lack that label. Alternatively or additionally, greyscaling can be combined with use of several optically distinguishable labels. For example, some nucleotide analog species can be represented in an extension reaction as a mixture of nucleotides of the same type but having different labels. Such a configuration is exemplified in US Pat app. Pub. No. 2013/0079232 A1 or 2015/0031560 A1, each of which is incorporated herein by reference.

Alternatively or additionally to the use of multiple different labels, greyscaling, and/or unlabeled species, an embodiment set forth herein can use a nucleotide analog having a ligand, cleavable linker or other moiety that provides for gain or loss of a label due to a defined treatment. Reagent systems of this type are illustrated in US Pat App. Pub. Nos. 2013/0079232 A1 or 2015/0031560 A1 where some nucleotide analog species have a ligand such that they can be distinguished from other nucleotide analogs based on initial absence of a detectable signal followed by appearance of a signal after treatment with an appropriately labeled receptor. These references also illustrate use of a nucleotide analog that can be distinguished based on an initial detectable signal that is subsequently lost, or at least reduced, due to treatment with a reagent that modifies the label (e.g. via chemical cleavage of a linker between the label and nucleotide moieties). In this case the other nucleotide analog species in the set are not susceptible to the modification (e.g. lacking the cleavable linker) and are distinguished based on persistence of signal generation after the treatment.

As exemplified above, in some embodiments, a label can be attached to a nucleotide analog via a cleavable linker. In particular embodiments, photocleavable linkers can be used in place of the chemically cleavable linker exemplified above. In some embodiments, the linker is selected from acid labile linkers (including dialkoxybenzyl linkers, Sieber linkers, indole linkers, t-butyl Sieber linkers), electrophilically cleavable linkers, nucleophilically cleavable linkers, photocleavable linkers, linkers that are cleaved under reductive conditions or oxidative conditions, safety-catch linkers, and linkers that are cleaved by elimination mechanisms. In some such embodiments, the linker is selected from a disulfide linker (—S—S—), ester, nitrobenzene, imine, enzymatically or chemically cleavable peptide and polynucleotide, such as DNA.

In some embodiments, members of a first set of nucleotide analogs (e.g. nucleotide analogs that are selectively deblocked by a first common treatment) used in a primer extension reaction will include only one type of optical label that gets detected and a second set of nucleotide analogs (e.g. nucleotide analogs that are selectively deblocked by a second common treatment), that is orthogonal to the first set will also include only one type of optical label that gets detected, wherein the label used in the first set is optically distinguishable from the label used in the second set. In this embodiment, the one type of optical label can be attached to substantially all of the nucleotide analogs of a first species in the first set, the one type of optical label can be attached to a subset of the nucleotide analogs of a second species in the first set, substantially all of the nucleotide analogs of a third species in the first set can be attached to a ligand, and substantially all of the nucleotide analogs of a fourth species in the first set are not attached to the one type of optical label or to the ligand.

In another embodiment, members of a first set of nucleotide analogs (e.g. nucleotide analogs that are selectively deblocked by a first common treatment) used in a primer extension reaction will include only two types of optical labels that get detected and a second set of nucleotide analogs (e.g. nucleotide analogs that are selectively deblocked by a second common treatment), that is orthogonal to the first set will also include only two types of optical label that get detected. In this embodiment, a first of the two types of optical labels can be attached to substantially all of the nucleotide analogs of a first species in the first set, a second of the two types of optical labels can be attached to substantially all of the nucleotide analogs of a second species in the first set, the first of the two types of optical labels and the second of the two types of optical labels can be attached to nucleotide analogs of a third species in the first set, and substantially all of the nucleotide analogs of a fourth species in the first set are not attached to the one of the two types of optical labels or the second of the two types of optical labels.

It will be understood from the above examples, that reducing the number of different labels in an orthogonal detection system can provide the advantage of reducing the complexity of the detection device needed to distinguish addition of different nucleotides to a template-bound primer. However, in many embodiments this is achieved by increasing the complexity of the fluidic steps such that the number of fluidic manipulations used during detection steps is increased compared to the fluidic steps used when each of the nucleotide species has a unique label. A general advantage of the present methods is that one skilled in the art can select an appropriate combination of labels, fluidic steps and detection devices to suit a particular application or circumstance.

As exemplified by the embodiments set forth above, in some cases two or more primers that are hybridized to two or more different nucleic acid templates, respectively, at a site can be simultaneously present during a primer extension step. Alternatively, a first of two primers that are hybridized to two or more different templates at a site can be removed from the site prior to extending a second of the two or more primers that are hybridized to the two or more different templates at the site.

Furthermore, two or more different primer extension products that result from the above steps can be simultaneously present at a site during a detection step. Alternatively, a first of two or more different primer extension products can be removed from a site prior to detecting a second of the two or more different primer extension products at the site.

Further still, two or more primer extension products, each having different reversible blocking moieties, can be simultaneously present during a deblocking step. The deblocking step can be configured to selectively remove (or otherwise modify) one or only a subset of the different reversible blocking moieties, such that at least one other reversible blocking moiety is retained (or unmodified) following the treatment. Alternatively, the different reversible blocking moieties that are simultaneously present can all be removed, for example, using a combination of deblocking treatments or a universal deblocking treatment. As a further alternative, a first of two or more different primer extension products can be removed from a site prior to subjecting a second of the two or more primer extension products with a deblocking treatment.

The present disclosure provides reaction mixtures (also referred to herein as reagent systems) that include various combinations of components. In several cases reaction components and several combinations of the components are described in the context of exemplary methods, such as those set forth in the preceding paragraphs. It will be understood that the reaction mixtures and the components thereof need not be limited to use in the methods exemplified herein. Other uses are contemplated as well. Accordingly, the components can be assembled, in a variety of useful combinations, for example to create kits. The kits can be useful for storage, transportation or commercial transaction of the components set forth herein. The kits can optionally include instructions for carrying out one or more of the methods set forth herein.

In particular embodiments, this disclosure provides a method for sequencing nucleic acid templates that can include the steps of (a) providing an array of sites, wherein each site includes a first nucleic acid template and a second nucleic acid template, wherein the first nucleic acid template has a sequence that is different from the sequence of the second nucleic acid template, wherein a first primer is bound to the first nucleic acid template, a reversible blocking moiety being attached to the first primer, wherein a second primer is bound to the second nucleic acid template, a reversible blocking moiety being attached to the second primer, and wherein the reversible blocking moiety that is attached to the first primer is different from the reversible blocking moiety that is attached to the second primer; (b) selectively removing the reversible blocking moiety that is attached to the first primer while retaining the reversible blocking moiety that is attached to the second primer; (c) extending the first primer by addition of a first nucleotide analog that is attached to a reversible blocking moiety; (d) selectively removing the reversible blocking moiety that is attached to the second primer while retaining the reversible blocking moiety that is attached to the nucleotide analog that is added to the first primer; (e) extending the second primer by addition of a second nucleotide analog that is attached to a reversible blocking moiety, wherein the reversible blocking moiety that is attached to the first nucleotide analog is different from the reversible blocking moiety that is attached to the second nucleotide analog; and (f) detecting the nucleotide analog that is added to the first primer and the nucleotide analog that is added to the second primer, at each of the sites, thereby determining the different sequences of the first template and the second template at each of the sites.

In some embodiments, the above method can further include steps of (g) selectively removing the reversible blocking moiety that is attached to the first nucleotide analog that is added to the first primer while retaining the reversible blocking moiety that is attached to the second nucleotide analog that is added to the second primer; (h) extending the first primer, after (g), by addition of a third nucleotide analog that is attached to a reversible blocking moiety; (i) selectively removing the reversible blocking moiety that is attached to the second nucleotide analog that is added to the second primer while retaining the reversible blocking moiety that is attached to the first nucleotide analog that is added to the first primer; (j) extending the second primer, after (i), by addition of a fourth nucleotide analog that is attached to a reversible blocking moiety, wherein the reversible blocking moiety that is attached to the third nucleotide analog is different from the reversible blocking moiety that is attached to the fourth nucleotide analog; and (k) detecting the nucleotide analog that is added to the first primer in (h) and the nucleotide analog that is added to the second prime in (j), at each of the sites, thereby determining the different sequences of the first template and the second template at each of the sites. Optionally, steps (g) through (k) can be repeated.

It will be understood that the steps set forth in the above embodiment and other embodiments of the present disclosure, need not follow the exemplified order. Taking as an example the embodiment in the preceding paragraphs, step (f), which recites a detection activity, need not occur after step (e). Rather, a first primer that is extended in step (c) can be detected prior to extending a second primer in step (d). Generally, a detection step can occur before or after one or more different reversible blocking moieties are removed.

The order of other steps can be changed to suit particular applications of the methods. An example of two methods that can employ similar steps, but in different orders is demonstrated by comparison of the cycle diagrams in FIG. 1 and FIG. 2. In the cycle diagram of FIG. 1 labels on primer extension products are detected prior to both deblocking and cleavage of the labels. Deblocking and label cleavage for nucleotides within each set are shown as happening simultaneously, which can be convenient, for example, when both are susceptible to the same treatment or due to compatible treatments. However, it is possible for deblocking and label cleavage to occur separately. As exemplified by the cycle diagram of FIG. 2, label cleavage and deblocking occur separately. In this example, the different labels that are present across the two different reactions (i.e. R1 and R2) are cleaved simultaneously. This is convenient, for example, when both types of labels can be cleaved using the same treatment or using compatible treatments. Comparison of the cycle diagrams in FIG. 1 and FIG. 2 illustrate other differences as well. For example, in FIG. 1, deblocking of the extension products of both reactions (R1 and R2) occurs after the detection step of the previous cycle, whereas in FIG. 2, the R2 extension product is deblocked prior to the detection step of the previous cycle and the R1 extension product is deblocked after the detection step of the previous cycle. There are a variety of different arrangements and orders of steps that can be used in a method set forth herein. Those skilled in the art will be able to readily determine a desirable arrangement and order based on the teaching set forth herein and known reactive characteristics of the reagents employed.

Furthermore, as exemplified previously herein the steps of the methods set forth herein can be carried out sequentially or simultaneously. For example, the selective removal of different reversible blocking moieties (e.g. steps (b) and (d) in the preceding paragraphs) can be carried out simultaneously or sequentially. Similarly, the extension of different primers (e.g. steps (c) and (e) in the preceding paragraphs), that have been deblocked using respective different deblocking treatments, can occur simultaneously or sequentially.

Universal priming sites are particularly useful for multiplex applications of the methods set forth herein. A universal priming site provides a region of sequence that is common to two or more nucleic acid molecules where the molecules also have different sequences in their template regions. A universal priming sequence present in different members of a collection of molecules can allow the replication, amplification or detection of multiple different sequences using a single universal primer species that is complementary to the universal sequence. Examples of methods of attaching universal sequences to a collection of target nucleic acids can be found in US Pat. App. Pub. No. 2007/0128624 A1, which is incorporated herein by reference.

In embodiments of the present disclosure, a first primer can have a first universal primer sequence that is complementary to a first universal priming site for a first template at a site. The same universal priming site can be present for a variety of different first templates at different sites of an array. Thus a single species of first universal primer can be used to amplify or extend the different first templates at the sites. Continuing with this example, a second primer can have a second universal primer sequence that is complementary to a second universal priming site for a second template at the site where the first template is also located. The same second universal priming site can be present for a variety of different second templates at the different sites of the array. Thus, a single species of second universal primer can be used to amplify or extend the different second templates at the sites.

An orthogonal sequencing method set forth herein can be utilized in a paired-end sequencing approach. Generally, paired end sequencing involves determining the sequences at two ends of a template sequence region, wherein the length of the template sequence region is known. Methods for fragmenting a target nucleic acid sample (e.g. genomic DNA sample), attaching primers to accommodate paired end reads and reading sequence from the ends of the fragments are known and can be carried out as described, for example, in U.S. Pat. Nos. 7,754,429; 8,017,335 or 8,192,930, each of which is incorporated herein by reference.

In the case of a sequencing-by-synthesis embodiment, nucleic acid fragments can be constructed to have two template sequences and paired reads can be obtained from each of the two templates to obtain 4 reads from a single fragment. An exemplary construct for obtaining 4 reads from a single fragment and methods for making the construct are set forth in US Pat. App. Pub. No. 2015/0031560 A1, which is incorporated herein by reference.

The present disclosure further provides a nucleic acid array that includes a plurality of sites on a solid support, wherein each site includes a first nucleic acid template and a second nucleic acid template, wherein the first nucleic acid template has a sequence that is different from the sequence of the second nucleic acid template, wherein a first primer is bound to the first nucleic acid template, a first reversible blocking moiety being attached to the first primer, wherein a second primer is bound to the second nucleic acid template, a second reversible blocking moiety being attached to the second primer, and wherein the first reversible blocking moiety is different from the second reversible blocking moiety. The nucleic acid array can further include one or more of the components described in the context of methods of the present disclosure. Products that inherently result from the methods set forth herein are also intended to be considered as components of a nucleic acid in some embodiments.

In particular embodiments, a nucleic acid array will include a first polymerase that is bound to the first primer and the first nucleic acid template at a site. Additionally, a second polymerase can be bound to the second primer and the second nucleic acid template at the site. In some cases, the first polymerase and second polymerase are the same species of polymerase. However, it can also be useful in some embodiments, for the first and second polymerases to be different species (e.g. a DNA polymerase and an RNA polymerase).

A nucleic acid array of the present disclosure can be present in a detection apparatus such as a nucleic acid sequencing apparatus. Exemplary detection apparatus are described herein and in references that are incorporated herein by reference. Generally, a detection apparatus can include a nucleic acid array and a detector that is positioned to detect one or more sites in the array. Typically, the detector will have a spatial resolution that is too low to resolve points at distance equivalent to the spacing between the first primer and the second primer at each of the sites. However, the use of orthogonal primer deblocking and extension allows the two primers to be resolved. The detector can be configured to observe any of a variety of signals as exemplified herein. For example, in some embodiments the detector is an optical detector. The sites of the array can have optical labels that are detectable by the optical detector. Different primers at each site can be extended to incorporate different optical labels and the optical detector can be configured to optically distinguish the different labels (e.g. due to differences in wavelength of light absorption, wavelength of luminescence excitation or wavelength of luminescence emission). In some configurations, a pixel of the detector is configured to simultaneously acquire signals from the first primer and the second primer.

Throughout this application various publications, patents or patent applications have been referenced. The disclosure of these publications in their entireties are hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method for sequencing nucleic acid templates, comprising
   (a) providing an array comprising a plurality of sites, wherein each site comprises a first nucleic acid template and a second nucleic acid template, wherein the first nucleic acid template has a sequence that is different from the sequence of the second nucleic acid template, wherein a first primer is bound to the first nucleic acid template, a reversible blocking moiety being attached to the first primer, wherein a second primer is bound to the second nucleic acid template, a reversible blocking moiety being attached to the second primer, and wherein the reversible blocking moiety that is attached to the first primer is different from the reversible blocking moiety that is attached to the second primer;
   (b) selectively removing the reversible blocking moiety that is attached to the first primer while retaining the reversible blocking moiety that is attached to the second primer;
   (c) extending the first primer by addition of a first nucleotide analog that comprises a reversible blocking moiety;
   (d) selectively removing the reversible blocking moiety that is attached to the second primer while retaining the reversible blocking moiety of the nucleotide analog that is added to the first primer;
   (e) extending the second primer by addition of a second nucleotide analog that comprises a reversible blocking moiety, wherein the reversible blocking moiety of the first nucleotide analog is different from the reversible blocking moiety of the second nucleotide analog; and
   (f) detecting the nucleotide analog that is added to the first primer and the nucleotide analog that is added to the second primer, at each of the sites, thereby determining the different sequences of the first template and the second template at each of the sites in an orthogonal manner by using a selective deblocking of nucleotides.

2. The method of claim 1, further comprising
   (g) selectively removing the reversible blocking moiety of the first nucleotide analog that is added to the first primer while retaining the reversible blocking moiety of the second nucleotide analog that is added to the second primer;
   (h) extending the first primer, after (g), by addition of a third nucleotide analog that comprises a reversible blocking moiety;
   (i) selectively removing the reversible blocking moiety of the second nucleotide analog that is added to the second primer while retaining the reversible blocking moiety of the first nucleotide analog that is added to the first primer;
   (j) extending the second primer, after (i), by addition of a fourth nucleotide analog that comprises a reversible blocking moiety, wherein the reversible blocking moiety of the third nucleotide analog is different from the reversible blocking moiety of the fourth nucleotide analog; and
   (k) detecting the nucleotide analog that is added to the first primer in (h) and the nucleotide analog that is added to the second prime in (j), at each of the sites, thereby determining the different sequences of the first template and the second template at each of the sites in an orthogonal manner by using a selective deblocking of nucleotides.

3. The method of claim 2, further comprising repeating steps (g) through (k).

4. The method of claim 1, wherein the detecting uses a detector having a spatial resolution that is too low to resolve points at distance equivalent to the spacing between the first primer and the second primer at each of the sites.

5. The method of claim 4, wherein the detector is an optical detector.

6. The method of claim 1, wherein the nucleotide analogs comprise optical labels.

7. The method of claim 6, wherein the first nucleotide analog is from a first set of nucleotide analogs, wherein the second nucleotide analog is from a second set of nucleotide analogs, and wherein the optical labels of the first set of nucleotide analogs are different from the optical labels of the second set of nucleotide analogs.

8. The method of claim 6, wherein the first nucleotide analog is from a first set of nucleotide analogs, wherein the second nucleotide analog is from a second set of nucleotide analogs, and wherein a subset of the nucleotide analogs in the first set of nucleotide analogs comprise optical labels.

9. The method of claim 8, wherein a subset of the nucleotide analogs in the second set of nucleotide analogs comprise optical labels.

10. The method of claim 9, wherein the subset of nucleotide analogs in the first set of nucleotide analogs comprise optical labels that are different from the optical labels of the subset of nucleotides in the second set of nucleotide analogs.

11. The method of claim 1, wherein the first nucleotide analog is from a first set of nucleotide analogs, wherein the second nucleotide analog is from a second set of nucleotide analogs, wherein the first set of nucleotide analogs comprise only one type of optical label that is detected in step (f) and the second set of nucleotide analogs comprise only one type of optical label that is detected in step (f).

12. The method of claim 11, wherein the one type of optical label is attached to substantially all of the nucleotide analogs of a first species in the first set, the one type of optical label is attached to a subset of the nucleotide analogs of a second species in the first set, substantially all of the nucleotide analogs of a third species in the first set are attached to a ligand, and substantially all of the nucleotide analogs of a fourth species in the first set are not attached to the one type of optical label or to the ligand.

13. The method of claim 1, wherein the first nucleotide analog is from a first set of nucleotide analogs, wherein the second nucleotide analog is from a second set of nucleotide analogs, wherein the first set of nucleotide analogs comprise only two types of optical labels that are detected in step (f) and the second set of nucleotide analogs comprise only two types of optical labels that are detected in step (f).

14. The method of claim 13, wherein only one of the two types of optical labels is attached to substantially all of the nucleotide analogs of a first species in the first set,
   only a second of the two types of optical labels is attached to substantially all of the nucleotide analogs of a second species in the first set, the one of the two types of optical labels and the second of the two types of optical labels are attached to nucleotide analogs of a third species in the first set, and substantially all of the nucleotide analogs of a fourth species in the first set are not attached to the one of the two types of optical labels or the second of the two types of optical labels.

15. The method of claim 4, wherein a pixel of the detector simultaneously acquires signals from both the first primer and the second primer.

16. The method of claim 1, wherein the first nucleic acid template comprises at least one base moiety that is the same species as a base moiety in the second nucleic acid template.

17. The method of claim 1, wherein steps (b) and (d) are carried out simultaneously.

18. The method of claim 1, wherein steps (b) and (d) are carried out sequentially.

19. The method of claim 1, wherein steps (c) and (e) are carried out simultaneously.

20. The method of claim 1, wherein steps (c) and (e) are carried out sequentially.

21. The method of claim 1, wherein a single nucleic acid molecule contains the first nucleic acid template and the second nucleic acid template.

22. The method of claim 1, wherein the first nucleic acid template and the second nucleic acid template are on different nucleic acid molecules.

23. The method of claim 1, wherein the sites have an area that is 100 $\mu m^2$ or less.

24. The method of claim 1, wherein the sites comprise multiple amplicons of the first nucleic acid template and multiple amplicons of the second nucleic acid template.

25. The method of claim 24, wherein the multiple amplicons comprise a nucleic acid cluster.

26. The method of claim 1, wherein the plurality of sites has a pitch of 10 $\mu m$ or less.

27. The method of claim 26, wherein the plurality of sites comprises at least $1 \times 10^6$ sites.

28. The method of claim 1, wherein each of the sites comprises a nucleic acid sequence that is unique compared to the nucleic acid sequences at the other sites in the plurality.

29. The method of claim 1, wherein the first primer comprises a first universal primer sequence and the first nucleic acid template at each site in the plurality of sites comprises a first universal primer binding sequence that is complementary to the first universal primer sequence.

30. The method of claim 29, wherein the second primer comprises a second universal primer sequence and the second nucleic acid template at each site in the plurality of sites comprises a second universal primer binding sequence that is complementary to the second universal primer sequence, wherein the first universal primer binding sequence is different from the second universal primer binding sequence.

31. The method of claim 1, wherein steps (c) and (e) are carried out by the same polymerase or the same species of polymerases.

32. The method of claim 1, wherein azidomethyl and tert-butoxy-ethoxy are used as reversible blocking moieties.

33. The method of claim 32, wherein the azidomethyl is selectively removed by phosphine treatment and the tert-butoxy-ethoxy is selectively removed by treatment with acid.

34. The method of claim 1, wherein the selective removal of the reversible blocking moieties comprise chemical treatment, heat treatment, irradiation or electrical treatment.

35. The method of claim 1, wherein the reversible blocking moiety that is attached to the first primer is the same species as the reversible blocking moiety that is attached to the first nucleotide analog.

36. The method of claim 35, wherein the reversible blocking moiety that is attached to the second primer is the same species as the reversible blocking moiety that is attached to the second nucleotide analog.

* * * * *